(12) United States Patent
Cho et al.

(10) Patent No.: US 7,388,101 B1
(45) Date of Patent: Jun. 17, 2008

(54) TETRAHYDROFURAN DERIVATIVES HAVING CIS SUBSTITUENT, THEIR INTERMEDIATES, AND THEIR PREPARATION METHOD

(75) Inventors: Yong Seo Cho, Seoul (KR); Hyunah Choo, Seoul (KR); Joo Hwan Cha, Seoul (KR); Ae Nim Pae, Seoul (KR); Satish N. Chavre, Seoul (KR); Kyung Il Choi, Seoul (KR)

(73) Assignee: Korea Institute of Science and Technology, Seoul (KR)

( * ) Notice: Subject to any disclaimer, the term of this patent is extended or adjusted under 35 U.S.C. 154(b) by 0 days.

(21) Appl. No.: 11/732,602

(22) Filed: Apr. 4, 2007

(51) Int. Cl.
*C07D 307/02* (2006.01)
(52) U.S. Cl. .................................................. 549/483
(58) Field of Classification Search ................. 549/483
See application file for complete search history.

(56) References Cited

OTHER PUBLICATIONS

Mukaiyama et al. STN Accession No. 1987:196150; Document No. 106:196150; Abstract of Chemistry Letters (1986), (7), 1157-60.*
Hopkins et al. STN Accession No. 1987:597967;.Document No. 107:197967 Journal of the American Chemical Society (1987), 109(15), 4748-9.*
Hopkins et al.STN Accession No. 1991:535825;Document No. 115:135825; Abstract of Journal of the American Chemical Society (1991) 113(14), 5354-65.*
Hopkins et al. .STN Accession No. 2006:646612;Document No. 145:292787; Abstract of Journal of the American Chemical Society (1992),114(25), 10093.*
Das et al. STN Accession No. 2003:965650 ; Document No. 140:145958; Abstract of Organic Letters (2004), 6(1), 123-126.*

Chavre et al. STN Accession No. 2006:646612;Document No. 145:292787; Abstract of Organic Letters (2006), 8(16), 3617-3619.*
Satish N. Chavre, et al., 5-Exocyclic Products, 2,3,5-Trisubstituted Tetrahydrofurans via Prins-Type Cyclization, Organic Letters, 2006, vol. 8, No. 16, pp. 3617-3619.
Andreou, Thanos et al.: << Synthesis of (—) Amphidinolide K Fragment C9-C22 >>, *Organic Letters* 2005, vol. 7, No. 19, pp. 4083-4086.
Ali, Mohammed A. et al.: << The First de Novo-Designed Antagonists of the Human $NK_2$ Receptor, *J. Med.Chem.* 2005, 48, pp. 5655-5658.

* cited by examiner

*Primary Examiner*—D. Margaret Seaman
*Assistant Examiner*—Nizal S Chandrakumar
(74) *Attorney, Agent, or Firm*—Frommer Lawrence & Haug LLP; Ronald R. Santucci

(57) ABSTRACT

The present invention relates to a tetrahydrofuran compound having cis substituents, the derivatives thereof and a process for preparing the same, and in particular relates to a dihydrofuran-3-ylidene triflate compound having cis substituents at $C_2$ and $C_5$ positions prepared through Prins-type cyclization using a homopropargylic alcohol derivative as a starting material in the presence of Lewis acid catalyst, a tetrahydrofuran compound having cis substituents at $C_2$, $C_3$ and $C_5$ positions prepared through the hydrolysis of triflate group in the derivatives of the dihydrofuran-3-ylidene triflate compound, and a preparation method thereof.

The derivatives and the target tetrahydrofuran compound prepared according to the present invention are hydrofuran compounds with novel structures having cis substituents at $C_2$, $C_3$ and/or $C_5$ positions, which are useful as a derivative for synthesizing drugs such as an antagonist for neurokinin receptor.

13 Claims, No Drawings

TETRAHYDROFURAN DERIVATIVES HAVING CIS SUBSTITUENT, THEIR INTERMEDIATES, AND THEIR PREPARATION METHOD

TECHNICAL FIELD

The present invention relates to a tetrahydrofuran compound having cis substituents, the derivatives thereof and a process for preparing the same and, in particular, relates to a dihydrofuran-3-ylidene triflate compound having cis substituents at $C_2$ and $C_5$ positions prepared through Prins-type cyclization using a homopropargylic alcohol derivative as a starting material in the presence of Lewis acid catalyst, a tetrahydrofuran compound having cis substituents at $C_2$, $C_3$ and $C_5$ positions prepared through the hydrolysis of triflate group in the derivatives of the dihydrofuran-3-ylidene triflate compound, and a preparation method thereof.

RELATED PRIOR ART

It has been known that a compound having cis substituents at $C_2$, $C_3$ and/or $C_5$ positions of a tetrahydrofuran cycle has superior pharmaceutical activities.

For example, various natural materials including (−)-amphidinolide have a tetrahydrofuran cycle with cis substituents substituted at $C_2$, $C_3$ and $C_5$ positions (*Org. Lett.* 2005, 7, 4083-4086). Recently, it was reported that a tetrahydrofuran compound having cis substituents at $C_2$, $C_3$ and $C_5$ positions may function as a neurokinin (NK) receptor antagonist within GPCR family, which has an therapeutic activity against a pain, an inflammation, Parkinson's disease and Alzheimer's disease (*J. Med. Chem.* 2005, 48, 5655-5658).

Therefore, a dihydrofuran-3-ylidene triflate compound having cis substituents at $C_2$ and $C_5$ positions prepared in the present invention as well as a tetrahydrofuran compound having cis substituents at $C_2$, $C_3$ and $C_5$ positions prepared by hydrolysis of the dihydrofuran-3-ylidene triflate compound may be usefully used in the synthesis of various natural materials and the development of new drugs.

An object of the present invention is to provide a novel dihydrofuran-3-ylidene triflate compound having cis substituents at $C_2$ and $C_5$ positions, and a preparation method thereof.

Another object of the present invention is to provide a novel tetrahydrofuran compound having cis substituents at $C_2$, $C_3$ and $C_5$ positions, and a preparation method thereof.

DETAILED DESCRIPTION OF INVENTION

The present invention relates to a dihydrofuran-3-ylidene triflate having cis substituents at $C_2$ and $C_5$ positions of the following Formula 1:

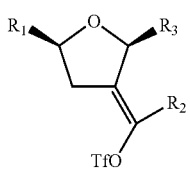

[Formula 1]

wherein $R_1$, $R_2$ and $R_3$ are a $C_1$-$C_{10}$ alkyl, a $C_1$-$C_{10}$ alkoxy $C_1$-$C_{10}$ alkyl, a benzoyloxy $C_1$-$C_{10}$ alkyl, an aryl $C_1$-$C_{10}$ alkyl or an aryl group, respectively; the aryl group is a phenyl or a naphthyl group optionally substituted with a substituent selected from the group consisting of a halogen atom, an alkyl, an alkoxy, a cyano, a nitro and a phenoxy group; and OTf is a triflate group.

Further, a tetrahydrofuran compound having cis substituents at $C_2$, $C_3$ and $C_5$ positions, which the present aims to provide, may be represented by the following Formula 2:

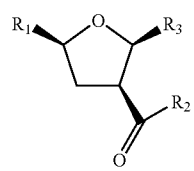

[Formula 2]

wherein $R_1$, $R_2$ and $R_3$ are same as defined in the above Formula 1.

Hereunder is provided a detailed description of the present invention.

A compound represented by Formula 1 or 2 is of a novel structure, and the structural characteristic lies in cis substituents substituted at $C_2$, $C_3$ and/or $C_5$ positions of hydrofuran cycles. Thus, a compound of Formula 1 or 2 according to the present invention may be usefully used in the field of medicine and fine chemistry and, in particular, the tetrahydrofuran compound of Formula 2 may be useful as a derivative for a drug.

As used herein, the term "alkyl" group refers to linear, branched or cyclic aliphatic saturated or unsaturated hydrocarbon having 1-10 carbons, preferably 1-8 carbons, more preferably 1-6 carbons, most preferably 1-4 carbons. Examples of the alkyl group include without limitation methyl, ethyl, n-propyl, isopropyl, butyl, isobutyl, t-butyl, cyclopropylmethyl, n-pentyl, neo-pentyl, cyclopentyl, cyclobutylmethyl, n-hexyl, isohexyl, cyclohexyl, cyclopentylmethyl, n-heptyl, isoheptyl, cycloheptyl, cyclohexylmethyl, n-octyl, isooctyl, cyclooctyl, n-nonyl, isononyl, cyclononyl, n-decanyl, isodecanyl, cyclodecanyl, benzyl and phenylethyl groups.

As used herein, the term "alkoxy" group refers to a hydroxyl, of which a hydrogen atom is substituted with the aforedefined alkyl group. Examples of the alkoxy group include without limitation methoxy, ethoxy, n-propoxy, i-propoxy, n-butoxy, i-butoxy, t-butoxy, benzyloxy and phenylethoxy groups.

As used herein, the term "aryl" group includes a monocyclic hydrocarbon having at least 6 members or a bicyclic hydrocarbon having at least 10 members or an aromatic cycle, which in the resonance-stabilized state through conjugated double bonds of adjacent carbon atoms. Examples of the aryl group include without limitation phenyl and naphthyl groups. The aryl group may comprise 1-4 substituents selected from the group consisting of a halogen atom, a $C_1$-$C_6$ alkyl, a $C_1$-$C_6$ alkoxy, a cyano, a nitro and a phenoxy group.

Preferably, in Formula 1 or 2:

$R_1$, $R_2$ and $R_3$ are a $C_1$-$C_8$ alkyl, a $C_1$-$C_8$ alkoxy $C_1$-$C_8$ alkyl, a $C_1$-$C_8$ alkoxy $C_1$-$C_8$ alkyl, a benzoyloxy $C_1$-$C_8$ alkyl, a phenyl $C_1$-$C_8$ alkyl, a phenyl or a naphthyl group, respectively; and the phenyl group is optionally substituted with a halogen atom or a nitro group.

More preferably, in Formula 1 or 2:

$R_1$, $R_2$ and $R_3$ are an aryl group, respectively;

$R_1$ and $R_3$ are a benzoyloxy alkyl or an aryl group, respectively, and $R_2$ is an alkyl, an arylalkyl or alkoxyalkyl group;

$R_1$ is a benzoyloxyalkyl or an aryl group; and $R_2$ and $R_3$ are an alkyl, an arylalkyl or an alkoxyalkyl group, respectively; and $R_1$ and $R_2$ are an alkyl, an arylalkyl or an alkoxyalkyl group, respectively, and $R_3$ is an aryl group.

The aryl group may be a substituted or non-substituted phenyl or a naphthyl group.

Further, the present invention also relates to a process for preparing a compound of Formula 1 or 2.

According to a process herein, as shown in Scheme 1, a dihydrofuran-3-ylidene triflate compound of Formula 1 or a tetrahydrofuran compound of Formula 2 may be prepared by performing Prins-type cyclization between homopropargylic alcohol derivative of Formula 3 and aldehyde derivative of Formula 4 in the presence of a Lewis acid.

The hydrolysis may be an acid hydrolysis or an alkali hydrolysis, which are normally employed. In the hydrolysis, typical organic solvents may also be used such as diethylether, tetrahydrofuran, methylene chloride, chloroform and ethyl acetate. Among these solvents, diethylether is preferred.

As described above, a process according to the present invention is a process for preparing cis-2,5-dihydrofuran-3-ylidene triflate compound and cis-2,3,5-tetrahydrofuran compound, where the stereochemistry of one carbon determines the stereochemistry of the other carbons through Prins-type cyclization. Further, the Prins-type cyclization employed in the present invention may be widely applied to the synthesis of chiral compounds in that (i) the process is simple, (ii) stereoselectivity is high, and (iii) the reaction condition is mild. Moreover, a compound according to the present invention is highly likely to be used as a derivative for natural materials and drugs in the field of medicine and fine chemistry.

[Scheme 1]

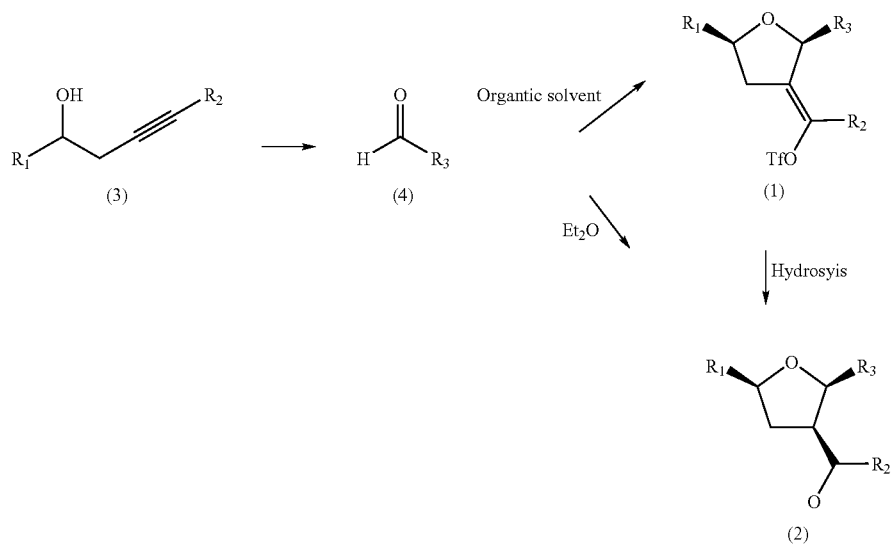

wherein $R_1$, $R_2$, $R_3$, and OTf are same as defined in Formula 1.

In the Prins-type cyclization, the Lewis acid is preferred to be trimethylsilyl trifluoromethanesulfonate (TMSOTf), and may be used in the amount of 1.0-4 equivalents, preferably 2-3 equivalents relative to homopropargylic alcohol derivative of Formula 3, i.e., one of starting materials.

The Prins-type cyclization is preferred be performed at a temperature of from −78° C. to room temperature (25° C.) for about 3-5 hours.

In the Prins-type cyclization, typical organic solvents may also be used such as diethylether, tetrahydrofuran, methylene chloride, chloroform and ethyl acetate. However, the present inventors ascertained an unexpected fact that, instead of a compound of Formula 1, a compound of Formula 2 may be obtained without performing hydrolysis through Prins-type cyclization by selecting diethylether as a solvent under the same reaction conditions except the solvent.

Further, a dihydrofuran-3-ylidene triflate compound of Formula 1 may be transformed into a tetrahydrofuran compound of Formula 2 by normal hydrolysis.

EXAMPLES

The present invention is described more specifically by the following Examples. Examples herein are meant only to illustrate the present invention, however, they should not be construed as limiting the scope of the claimed invention.

Example 1

Preparation of (E)-1-(cis-2-(4-nitrophenyl)-5-phenyl-dihydrofuran-3(2H)-ylidene)-ethyl trifluoromethane-sulfonate

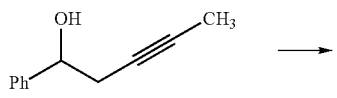

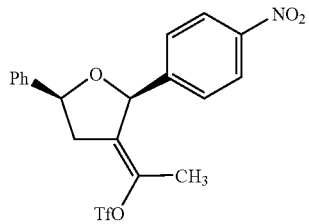

1-Phenylpent-3-yn-1-ol (50 mg, 0.31 mmol) and 4-nitrobenzaldehyde (0.057 mg, 0.37 mmol) were dissolved in methylene chloride (3.0 mL). After the temperature was lowered to −78° C., trimethylsilyl trifluoromethanesulfonate (TMSOTf) (170 mL, 0.93 mmol) was added, and the solution was stirred for one hour at the same temperature. The temperature was slowly elevated to room temperature for about 3 hours, and the solution was further stirred for another one hour at room temperature. The solution was added with an aqueous $NaHCO_3$ solution and diluted with diethylether. The organic layer was washed with water and brine, dried with $MgSO_4$, filtered and condensed. A pure target compound (31 mg) was obtained with a yield of 77% by using column chromatography.

$^1$H NMR (300 MHz, $CDCl_3$) δ 8.30 (d, 2H, J=8.8 Hz), 7.61 (d, 2H, J=8.7 Hz) 7.38-7.32 (m, 5H), 5.61 (s, 1H), 5.07 (dd, 1H, J=10.8, 5.1 Hz), 3.41 (dd, 1H, J=16.0, 5.1 Hz), 2.92-2.81 (m, 1H), 1.77 (s, 3H).

Example 2

Preparation of (E)-1-(cis-2,5-diphenyl-dihydrofuran-3(2H)-ylidene)ethyl trifluoromethanesulfonate

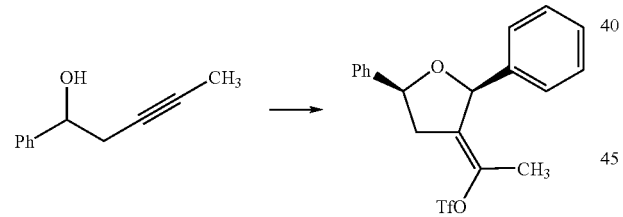

A target compound was obtained with a yield of 68% as described in Example 1 by using 1-phenylpent-3-yn-1-ol (50 mg, 0.31 mmol) and benzaldehyde (38 mL, 0.37 mmol).

$^1$H NMR (300 MHz, $CDCl_3$) δ 7.47-7.30 (m, 10H), 5.53 (s, 1H), 5.54 (dd, 1H, J=10.8, 5.1 Hz), 3.41 (dd, 1H, J=16.2, 5.1 Hz), 2.94-2.88 (m, 1H), 1.76 (s, 3H).

Example 3

(E)-1-(cis-2-(naphthalene-2-yl)-5-phenyl-dihydrofuran-3(2H)-ylidene)ethyl trifluoromethanesulfonate

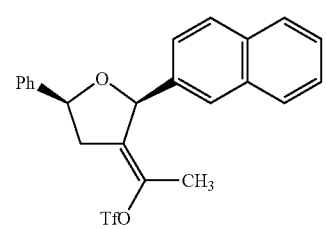

A target compound was obtained with a yield of 68% as described Example 1 by using 1-phenylpent-3-yn-1-ol (50 mg, 0.31 mmol) and 2-naphthalenealdehyde (56 mg, 0.37 mmol).

$^1$H NMR (300 MHz, $CDCl_3$) δ 7.98-7.90 (m, 4H), 7.59-7.47 (m, 3H), 7.47-7.30 (m, 5H,), 5.72 (s, 1H), 5.11 (dd, 1H, J=11.1, 5.4 Hz), 3.46 (dd, 1H, J=16.2, 5.1 Hz), 3.06-2.89 (m, 1H), 1.77 (s, 3H).

Example 4

Preparation of (E)-1-(cis-2-(4-chlorophenyl)-5-phenyl-dihydrofuran-3(2H)-ylidene)ethyl trifluoromethanesulfonate

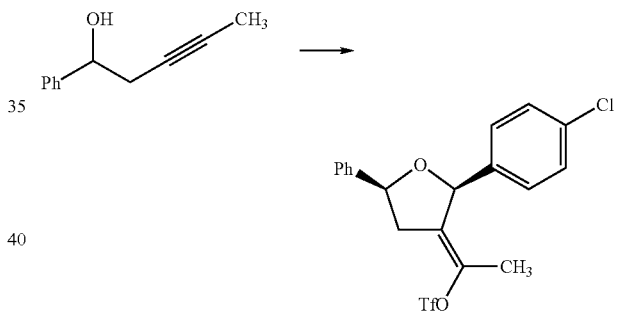

A target compound was obtained with a yield of 76% as described in Example 1 by using 1-phenylpent-3-yn-1-ol (50 mg, 0.31 mmol) and 4-chlorobenzaldehyde (53 mg, 0.37 mmol).

$^1$H NMR (300 MHz, $CDCl_3$) δ 7.50-7.26 (m, 12.5H), 5.48 (s, 1H), 5.23 (s, 0.16H), 5.01 (dd, 1H, J=10.8, 5.2 Hz), 4.90-3.81 (m, 0.16H), 3.36 (dd, 1H, J=16.0, 5.1 Hz), 2.87-2.79 (m, 1.16H), 2.68-2.37 (m, 0.16H), 1.73 (s, 3.5H).

Example 5

Preparation of (E)-1-(cis-2-(2-nitrophenyl)-5-phenyl-dihydrofuran-3(2H)-ylidene)ethyl trifluoromethanesulfonate

-continued

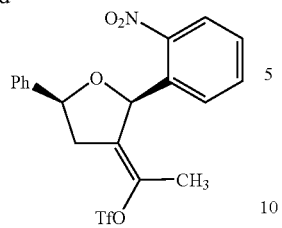

A target compound was obtained with a yield of 35% as described in Example 1 by using 1-phenylpent-3-yn-1-ol (50 mg, 0.31 mmol) and 2-nitrobenzaldehyde (56 mg, 0.37 mmol).

$^1$H NMR (300 MHz, CDCl$_3$) δ 7.90 (d, 1H, J=8.0 Hz), 7.71 (t, 1H, J=7.4 Hz), 7.61-7.54 (m, 2H), 7.36-7.32 (m, 5H), 6.18 (s, 1H), 5.03 (dd, 1H, J=10.7, 5.3 Hz), 3.41 (dd, 1H, J=16.1, 5.3 Hz), 2.92-2.82 (m, 1H), 1.81 (s, 3H).

Example 6

Preparation of (E)-1-(cis-2-methyl-5-phenyl-dihydrofuran-3(2H)-ylidene)ethyl trifluoromethanesulfonate

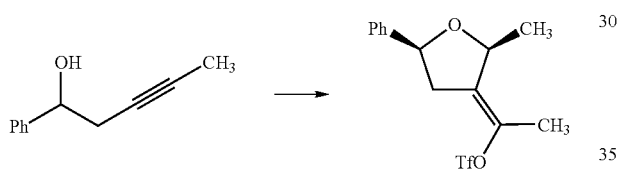

A target compound was obtained with a yield of 68% as described in Example 1 by using 1-phenylpent-3-yn-1-ol (50 mg, 0.31 mmol) and ethanal (35 mL, 0.62 mmol).

$^1$H NMR (300 MHz, CDCl$_3$) δ 7.42-7.30 (m, 5H), 4.86 (dd, 1H, J=10.9, 5.0 Hz), 4.76-4.72 (m, 1H), 3.15 (dd, 1H, J=15.6, 5.0 Hz), 2.66-2.56 (m, 1H), 2.09 (s, 3H), 1.49 (d, 3H, J=6.3 Hz).

Example 7

Preparation of (E)-1-(cis-2-ethyl-5-phenyl-dihydrofuran-3(2H)-ylidene)ethyl trifluoromethanesulfonate

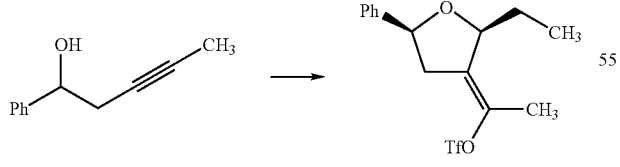

A target compound was obtained with a yield of 69% as described in Example 1 by using 1-phenylpent-3-yn-1-ol (50 mg, 0.31 mmol) and propanal (27 mL, 0.37 mmol).

$^1$H NMR (400 MHz, CDCl$_3$) δ 7.45-7.25 (m, 6H), 4.85 (dd, 1H, J=11.0, 5.0 Hz), 4.67 (br s, 1H), 4.51 (br s, 0.2H), 3.82-3.70 (m, 0.2H), 3.15 (dd, 1H, J=15.4, 5.0 Hz), 2.89-2.78 (m, 0.2H), 2.60-2.44 (m, 1H), 2.27-2.12 (m, 0.2H), 2.07 (s, 3H), 2.01 (s, 0.6H), 1.98-1.81 (m, 1H), 1.81-1.68 (m, 1.2H), 1.68-1.57 (m, 0.2H), 1.07 (t, 3H, J=7.4 Hz), 1.02-0.90 (m, 0.6H).

Example 8

Preparation of (E)-1-(cis-2-isopropyl-5-phenyl-dihydrofuran-3(2H)-ylidene)ethyl trifluoromethanesulfonate

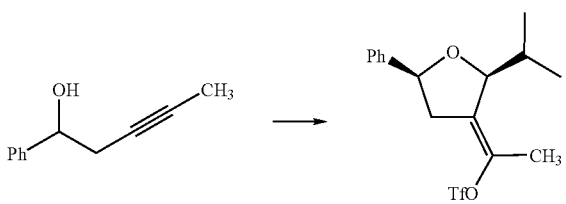

A target compound was obtained with a yield of 60% as described in Example 1 by using 1-phenylpent-3-yn-1-ol (50 mg, 0.31 mmol) and isobutanal (31 mL, 0.37 mmol).

$^1$H NMR (300 MHz, CDCl$_3$) δ 7.44-7.22 (m, 5H), 4.84 (dd, 1H, J=11.2, 4.9 Hz), 4.55 (s, 1H), 3.15 (dd, 1H, J=15.1, 4.8 Hz), 2.52-2.44 (m, 1H), 2.08 (s, 3H), 2.04-1.98 (m, 1H), 1.14 (d, 3H, J=6.9 Hz), 1.04 (d, 3H, J=6.8 Hz).

Example 9

Preparation of (E)-1-(cis-2-pentyl-5-phenyl-dihydrofuran-3(2H)-ylidene)ethyl trifluoromethanesulfonate

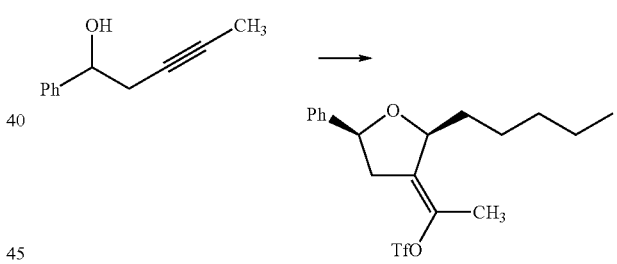

A target compound was obtained with a yield of 65% as described in Example 1 by using 1-phenylpent-3-yn-1-ol (50 mg, 0.31 mmol) and hexanal (45 mL, 0.37 mmol).

$^1$H NMR (400 MHz, CDCl$_3$) δ 7.40-7.26 (m, 5H), 4.85 (q, 1H, J=5.02 Hz, J=11.0 Hz), 4.68 (t, 1H), 3.14 (dd, 1H, J=4.9 Hz), 2.60-2.43 (m, 1H), 2.07 (s, 3H), 1.81-1.69 (m, 2H), 1.55-1.52 (m, 2H), 1.36-1.33 (m, 5H), 0.92 (t, 3H).

Example 10

Preparation of (E)-1-(cis-2-phenylethyl-5-phenyl-dihydrofuran-3(2H)-ylidene)ethyl trifluoromethanesulfonate

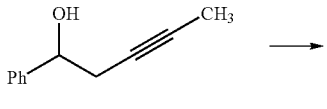

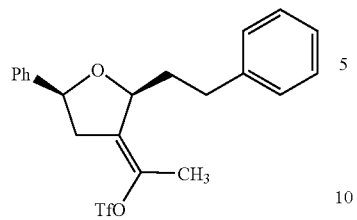

A target compound was obtained with a yield of 61% as described in Example 1 by using 1-phenylpent-3-yn-1-ol (50 mg, 0.31 mmol) and 3-phenylpropanal (49 mL, 0.37 mmol).

$^1$H NMR (400 MHz, CDCl$_3$) δ 7.50-7.17 (m, 12H), 4.89 (dd, 1H, J=11.0, 5.0 Hz), 4.69 (d, 1H, J=6.0 Hz), 4.56-4.48 (m, 0.2H), 3.92-9.83 (m, 0.2H), 3.16 (dd, 1H, J=5.0 Hz), 2.99-2.70 (m, 2.6H), 2.68-2.53 (m, 1H), 2.36-2.22 (m, 0.2H), 2.20-1.84 (m, 2.4H) 2.03 (s, 3H), 2.00 (s, 0.6H).

Example 11

Preparation of (E)-1-(cis-2-(4-nitrophenyl-5-phenyl-dihydrofuran-3(2H)-ylidene)ethyl trifluoromethanesulfonate

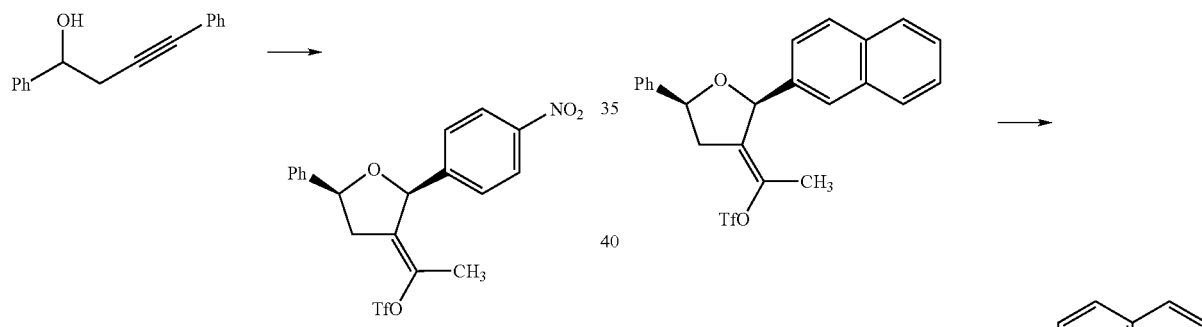

A target compound was obtained with a yield of 64% as described in Example 1 by using 1,4-diphenylbut-3-yn-1-ol (100 mg, 0.45 mmol) and 4-nitrobenzaldehyde (82 mg, 0.54 mmol).

$^1$HNMR (400 MHz, CDCl$_3$) δ 8.01 (d, 2H, J=6.8 Hz), 7.48-7.16 (m, 10H), 7.07 (d, 2H, J=7.1 Hz), 5.65 (d, 1H, J=1.9 Hz), 5.20 (dd, 1H, J=10.7, 5.3 Hz), 3.57 (dd, 1H, J=16.5, 5.5 Hz), 3.08 (ddd, 1H, J=16.5, 10.7, 2.2 Hz).

Example 12

Preparation of ((2R,5R,E)-5-phenyl-4-(1-(trifluoromethylsulfonyloxy)pentylidene)-tetrahydrofuran-2-yl)methyl benzoate

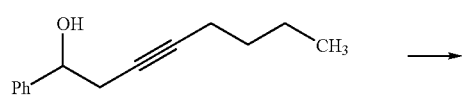

A target compound was obtained with a yield of 84% as described in Example 1 by using (R)-2-hydroxynon-4-ynyl benzoate (50 mg, 0.19 mmol) and benzaldehyde (25 mg, 0.23 mmol).

$^1$H NMR (300 MHz, CDCl$_3$) δ 8.05-8.02 (m, 2H), 7.60-7.55 (m, 1H), 7.48-7.42 (m, 2H), 7.37-7.33 (m, 5H), 5.46 (s, 1H), 4.67-4.54 (m, 1H). 4.50-4.35 (m, 2H). 3.13 (dd, 1H, J=10.9, 5.1 Hz). 2.92-2.76 (m, 1H), 2.04-1.92 (m, 2H), 1.38-1.21 (m, 2H), 1.16-0.94 (m, 2H), 0.75 (t, 3H, J=6.6 Hz).

Example 13

Preparation of 1-(cis-2-(naphthalene-2-yl)-5-phenyl-tetrahydrofuran-3-yl)ethanone (E)-1-(cis-2-(naphthalene-2-yl)-5-phenyl-dihydrofuran-3(2H)-ylidene)ethyl trifluoromethanesulfonate was dissolved in a solution containing 1,4-dioxane and methanol in a ratio of 2:1, treated with an aqueous NaOH solution (1%, 4 mL) at room temperature, and sufficiently stirred for 3 hours. After the reaction was completed, a saline solution was added and the solution was diluted with ethylacetate. The organic layer was washed with water, dried with Na$_2$SO$_4$, filtered and condensed. A pure target compound (16.5 mg) was obtained with a yield of 98% by using column chromatography.

$^1$H NMR (300 MHz, CDCl$_3$) δ 7.95-7.87 (m, 4H), 7.68-7.32 (m, 10H), 5.34 (d, 1H, J=7.5 Hz), 5.20 (t, 1H, J=7.8 Hz), 3.47-3.41 (m, 1H), 2.78-2.71 (m, 1H), 2.38-2.30 (m, 1H), 2.17 (s, 3H).

Example 14

Preparation of (cis-2-(4-nitrophenyl)-5-phenyl-tetrahydrofuran-3-yl)(phenyl)methanone

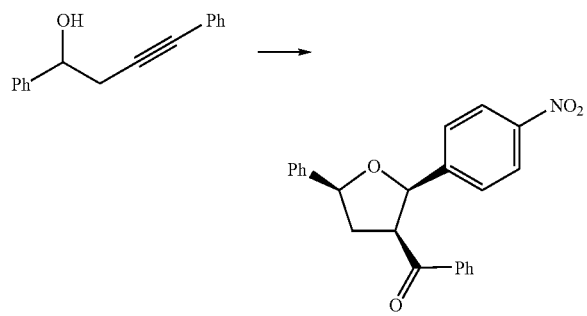

1,4-Diphenylbut-3-yn-1-ol (50 mg, 0.23 mmol) and 4-nitrobenzaldehyde (41 mg, 0.27 mmol) were dissolved in diethylether (3.0 mL). After the temperature was lowered to −78° C., trimethylsilyl trifluoromethanesulfonate (TMSOTf) (90 mL, 0.50 mmol) was added, and the solution was stirred for one hour at the same temperature. The temperature was slowly elevated to room temperature for about 3 hours, and the solution was further stirred for additional one hour at room temperature. The solution was added with an aqueous NaHCO$_3$ solution and diluted with diethylether. The organic layer was washed with water and brine, dried with MgSO$_4$, filtered and condensed. A pure target compound (31 mg) was obtained with a yield of 35% by using column chromatography.

$^1$H NMR (400 MHz, CDCl$_3$) δ 7.91 (d, 2H), 7.63-7.60 (m, 4H), 7.47-7.44 (m, 3H), 7.37-7.34 (m, 3H), 7.27-7.26 (m, 1H), 5.53 (d, 1H, J=9.1 Hz) 5.17 (dd, 1H, J=10.4, 5.7 Hz), 4.72 (q, 1H, J=8.2 Hz), 2.82-2.75 (m, 1H), 2.63-2.56 (m, 1H).

Example 15

Preparation of 1-(cis-2-(4-nitrophenyl)-5-phenyl-tetrahydrofuran-3-yl)-ethanone

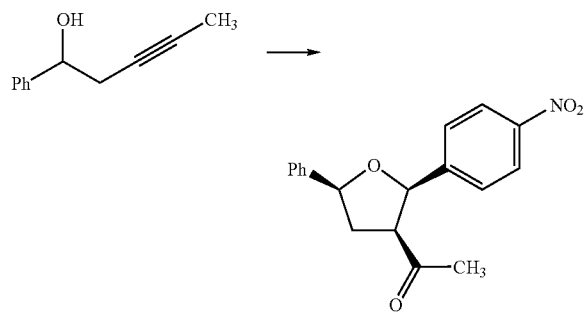

A target compound was obtained with a yield of 41% as described in Example 14 by using 1-phenylpent-3-yn-1-ol (50 mg, 0.31 mmol) and 4-nitrobenzaldehyde (56 mg, 37 mmol).

$^1$H NMR (400 MHz, CDCl$_3$) δ 8.30-8.14 (m, 2H), 7.68-7.54 (m, 2H), 7.45-7.26. (m, 5H), 5.37 (d, 1H, J=7.5 Hz), 5.12 (t, 1H, J=8.23 Hz), 3.24-2.21 (m, 1H), 2.62-2.59 (m, 1H), 2.40-2.27 (m, 1H), 2.21 (s, 3H).

Example 16

Preparation of 1-(cis-2,5-diphenyl-tetrahydrofuran-3-yl)-ethanone

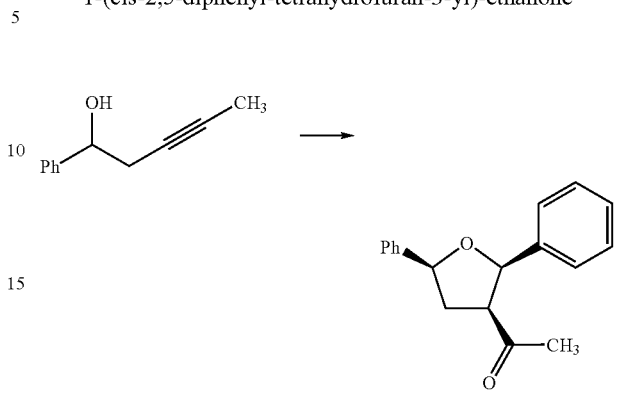

A target compound was obtained with a yield of 38% as described in Example 14 by using 1-phenylpent-3-yn-1-ol (50 mg, 0.31 mmol) and benzaldehyde (28 mL, 37 mmol).

$^1$H NMR (400 MHz, CDCl$_3$) δ 7.52-7.26 (m, 10H), 5.15-5.09 (m, 2H), 3.35-3.30 (m, 1H), 2.70-2.64 (m, 1H), 2.27-2.19 (m, 1H), 2.14 (s, 3H).

Example 17

Preparation of 1-(cis-2-methyl-5-phenyl-tetrahydrofuran-3-yl)-ethanone

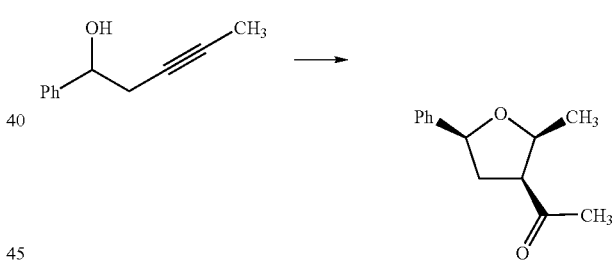

A target compound was obtained with a yield of 30% as described in Example 14 by using 1-phenylpent-3-yn-1-ol (50 mg, 0.31 mmol) and ethanal (35 mL, 62 mmol).

$^1$H NMR (400 MHz, CDCl$_3$) δ 7.41-7.25 (m, 5H), 4.95 (t, 1H, J=7.4 Hz), 4.23 (quin, 1H, J=6.4 Hz), 2.94-2.89 (m, 1H), 2.60-2.53 (m, 1H), 2.23 (s, 3H), 2.12-2.04 (m, 1H), 1.47 (d, 3H, J=6.0 Hz).

Example 18

Preparation of 1-(cis-2-isopropyl-5-phenyl-tetrahydrofuran-3-yl)-ethanone

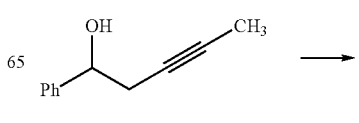

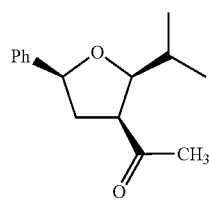

A target compound was obtained with a yield of 18% as described in Example 14 by using 1-phenylpent-3-yn-1-ol (50 mg, 0.31 mmol) and isobutanal (31 mL, 37 mmol).

$^1$H NMR (300 MHz, CDCl$_3$) δ 7.37-7.27 (m, 5H), 4.92 (dd, 1H, J=9.3, 6.3 Hz), 4.07-4.02 (m, 1H), 3.11-3.05 (m, 1H), 2.46-2.39 (m, 1H), 2.26 (s, 3H), 1.98-1.89 (m, 2H), 1.07 (d, 3H, J=6.6 Hz), 1.00 (d, 3H, J=6.8 Hz).

As described above, the present invention has the following characteristics:

(i) a dihydrofuran-3-ylidene triflate compound having cis substituents at C$_2$ and C$_5$ positions in various structures may be prepared through Prins-type cyclization by using a homopropargylic alcohol derivative as a starting material;

(ii) a tetrahydrofuran compound having cis substituents at C$_2$, C$_3$ and C$_5$ positions, which is widely used as a derivative for natural materials or drugs, may be prepared by hydrolysis of thus prepared dihydrofuran-3-ylidene triflate compound; and (iii) a tetrahydrofuran compound having cis substituents at C$_2$, C$_3$ and C$_5$ positions may be prepared in diethylether solvent through Prins-type cyclization by using a homopropargylic alcohol derivative as a starting material. Therefore, a compound or a process according to the present invention is expected to be usefully used in the field of medicine and fine chemistry.

What is claimed is:

1. A dihydrofuran-3-ylidene triflate having cis substituents at C$_2$ and C$_5$ positions of the following Formula 1:

[Formula 1]

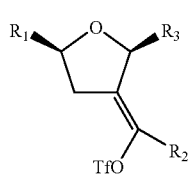

wherein R$_1$, R$_2$ and R$_3$ are a C$_1$-C$_{10}$ alkyl, a C$_1$-C$_{10}$ alkoxy C$_1$-C$_{10}$ alkyl, a benzoyloxy C$_1$-C$_{10}$ alkyl, an aryl C$_1$-C$_{10}$ alkyl or an aryl group, respectively; the aryl group is a phenyl or a naphthyl group optionally substituted with a substituent selected from the group consisting of a halogen atom, an alkyl, an alkoxy, a cyano, a nitro and a phenoxy group; and OTf is a triflate group.

2. The compound of claim 1, wherein R$_1$, R$_2$ and R$_3$ are a C$_1$-C$_8$ alkyl, a C$_1$-C$_8$ alkoxy C$_1$-C$_8$ alkyl, a benzoyloxy C$_1$-C$_8$ alkyl, an phenyl C$_1$-C$_8$ alkyl, a phenyl or a naphthyl group, respectively; and the phenyl group is optionally substituted with a halogen atom or a nitro group.

3. The compound of claim 1, wherein R$_1$, R$_2$ and R$_3$ are an aryl group, respectively.

4. The compound of claim 1, wherein R$_1$ and R$_3$ are a benzoyloxy alkyl or an aryl group, respectively; and R$_2$ is an alkyl, an arylalkyl or alkoxyalkyl group.

5. The compound of claim 1, wherein R$_1$ is a benzoyloxy-alkyl or an aryl group; and R$_2$ and R$_3$ are an alkyl, an arylalkyl or alkoxyalkyl group, respectively.

6. The compound of claim 1, wherein R$_1$ and R$_2$ are an alkyl, an arylalkyl or alkoxyalkyl group, respectively; and R$_3$ is an aryl group.

7. A process for preparing a dihydrofuran-3-ylidene triflate compound of Formula 1, which comprises the step of performing Prins-type cyclization between homopropargylic alcohol derivative of the following Formula 3 and aldehyde derivative of the Formula 4 in a solvent selected from the group consisting of methylene chloride and chloroform and in the presence of a Lewis acid of trimethylsilyl trifluoromethanesulfonate (TMSOTf), whereby preparing a dihydrofuran-3-ylidene triflate compound of the following Formula 1 having cis-oriented substituents at C$_2$ and C$_5$ positions:

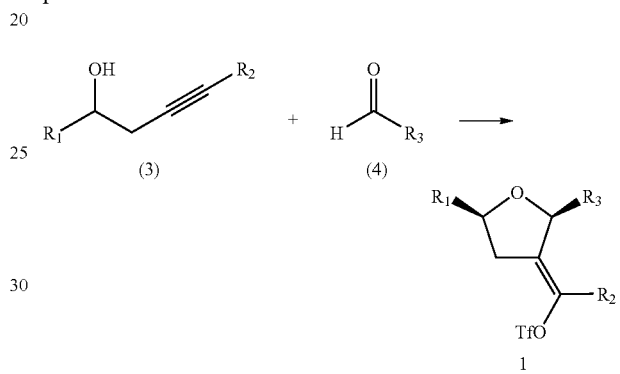

wherein R$_1$, R$_2$ and R$_3$ are a C$_1$-C$_{10}$ alkyl, a C$_1$-C$_{10}$ alkoxy C$_1$-C$_{10}$ alkyl, a benzoyloxy C$_1$-C$_{10}$ alkyl, an aryl C$_1$-C$_{10}$ alkyl or an aryl group, respectively; the aryl group is a phenyl or a naphthyl group optionally substituted with a substituent selected from the group consisting of a halogen atom, an alkyl, an alkoxy, a cyano, a nitro and a phenoxy group; and OTf is a triflate group.

8. The process of claim 7, wherein the Lewis acid is used in the amount of 2.0-3.0 equivalents relative to the homopropargylic alcohol derivative.

9. The process of claim 7, wherein the Prins-type cyclization is performed at a temperature of from −78° C. to 25° C.

10. A process for the preparing a tetrahydrofuran compound of Formula 2, which comprises the step of performing a hydrolysis of a dihydrofuran-3-ylidene triflate compound of Formula 1 having cis-oriented substituents at C$_2$ and C$_5$ positions, whereby preparing a tetrahydrofuran compound of Formula 2 having cis-oriented substituents at C$_2$, C$_3$ and C$_5$ positions:

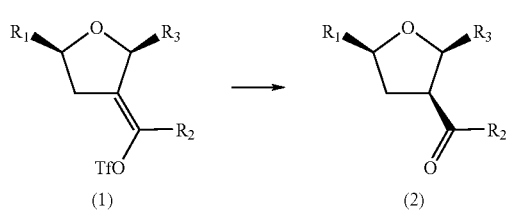

wherein $R_1$, $R_2$ and $R_3$ are a $C_1$-$C_{10}$ alkyl, a $C_1$-$C_{10}$ alkoxy $C_1$-$C_{10}$ alkyl, a benzoyloxy $C_1$-$C_{10}$ alkyl, an aryl $C_1$-$C_{10}$ alkyl or an aryl group, respectively; the aryl group is a phenyl or a naphthyl group optionally substituted with a substituent selected from the group consisting of a halogen atom, an alkyl, an alkoxy, a cyano, a nitro and a phenoxy group; and OTf is a triflate group.

11. The process of claim 10, wherein the hydrolysis is performed in diethylether solvent.

12. The process of claim 10, wherein the Lewis acid is used in the amount of 2.0-3.0 equivalents relative to the homopropargylic alcohol derivative.

13. The process of claim 10, wherein the Prins-type cyclization is performed at a temperature of from −78° C. to 25° C.

* * * * *